United States Patent [19]
Moore et al.

[11] Patent Number: 5,874,103
[45] Date of Patent: Feb. 23, 1999

[54] IONOPHORE ANTIBIOTIC FORMULATIONS

[75] Inventors: Derek George Moore, Auckland, New Zealand; Lionel Barry Lowe, Dural, Australia; Kevin Charles Palmer; Kim Ewing Melville Agnew, both of Auckland, New Zealand

[73] Assignee: Eli Lilly and Company, Indianapolis, Ind.

[21] Appl. No.: 685,121

[22] Filed: Jul. 23, 1996

[30] Foreign Application Priority Data

Sep. 6, 1995 [NZ] New Zealand ............................ 272940

[51] Int. Cl.⁶ ............................ A23K 1/18; A61K 31/35; A61K 31/695; A61K 47/00
[52] U.S. Cl. ............................ 424/438; 514/460; 514/63; 514/772; 514/782
[58] Field of Search ..................... 424/490, 438; 514/460, 63, 772, 782

[56] References Cited

U.S. PATENT DOCUMENTS

| | | | |
|---|---|---|---|
| 3,715,372 | 2/1973 | Stempel et al. | 549/414 |
| 3,829,557 | 8/1974 | Winfield | 423/478 |
| 4,746,349 | 5/1988 | Becker | 71/6 |
| 5,112,604 | 5/1992 | Beaurline et al. | 424/490 |
| 5,300,439 | 4/1994 | Charlton | 436/74 |

FOREIGN PATENT DOCUMENTS

| | | | |
|---|---|---|---|
| 0 405 930 | 1/1991 | European Pat. Off. | A61K 9/10 |
| 0 470 667 | 2/1992 | European Pat. Off. | A61K 31/495 |
| 0 556 057 | 8/1993 | European Pat. Off. | A61K 9/00 |
| 0 620 001 | 10/1994 | European Pat. Off. | A61K 9/00 |

*Primary Examiner*—Kevin E. Weddington
*Attorney, Agent, or Firm*—Edward P. Gray; Kathleen R. S. Page; Paul R. Cantrell

[57] ABSTRACT

An aqueous base suspension concentrate of an ionophore antibiotic or ionophore antibiotics capable of aqueous dilution (if desired) and capable (with or without such aqueous dilution) of being orally administered to an animal (eg; by drenching), said concentration comprising (I) at least one ionophore antibiotic in (II) an aqueous system containing ( ) a wetting and/or surfactant agent (ii) an antifreeze agent or agents in which the ionophore antibiotic or antibiotics is or are no more than sparingly soluble, (iii) a suspension agent, (iv) optionally an antifoam agent or system, (v) optionally a preservative, (vi) optionally a de-bittering agent, (vii) optionally a pH buffering system, and (viii) water.

38 Claims, 1 Drawing Sheet

Fig. 1

IONOPHORE ANTIBIOTIC FORMULATIONS

The present invention relates to an aqueous base suspension concentrate of an ionophore antibiotic or ionophore antibiotics capable with or without dilution of being administered to an animal.

Administration of ionophore antibiotics such as monensin to animals (preferably ruminants) is known to achieve in appropriate dosages advantages for a number of different purposes. These include the treatment or prevention of ketosis and/or bloat, the enhancement of milk production, enhancement of milk protein content in milk, enhancement of mineral uptake, enhancement of weight gain, and/or enhancement of feed conversion efficiency (in ruminants), desirable reproduction advantages and as a milk replacement. See U.S. Pat. No. 3,829,557.

In this respect we refer to European Patent Specification 0,139,595 A2 of KOFFOLK (1949) LTD which relates to a liquid ionophore antibiotic composition for ruminants and poultry where the antibiotic is dissolved in a non-toxic water-soluble organic solvent and in use the resulting solution is admixed with a liquid feed, a liquid vitamin concentrate or drinking water. There are claims for stability on standing even for long periods.

The composition of EP 0,139,595 indicates that because monensin and its sodium salt is only slightly soluble in water that it is generally administered in a dry form in an animal feed and/or in dry liquid milk replacer compositions. The same is also indicated as being true for another ionophore antibiotic lasalocid which in U.S. Pat. No. 3,715,372 is reported to be completely insoluble in water.

The composition of EP 0,139,595 uses as an organic solvent for the ionophore antibiotic a solvent selected from the group comprising propylene glycol, glycerol, ethanol and isopropanol and mixtures thereof.

Example 1 of EP 0,139,595 indicates that 250 g of a mycelium containing 10% monensin was mixed at room temperature with 1250 cc propylene glycol for 2 hours by exposing the mixture to ultrasound. There is an indication that 50% of the monensin was found in solution in the propylene glycol.

Monensin is usually available commercially as the sodium salt of the acid. Monensin sodium is available in two forms, namely, a crystalline form or a mycelial form. The mycelial form has only about a 20% activity while the crystalline form has greater than 90% active monensin sodium.

Reference herein to "monensin" where the context allows encompasses all forms thereof including monensin, alkali metal salts of monensin and monensin esters. Likewise for the other ionophore antibiotics.

We have found monopropylene glycol to be a poor solvent of monensin and therefore while we refer to monopropylene glycol as being an antifreeze agent in which the ionophore antibiotic is sparingly soluble we do appreciate that solubility to the extent referred to in Example 1 of EP 0,139,595 may be achieved when induced with ultrasound or heating.

We have found however that it is possible to include in an aqueous suspension system monopropylene glycol as an antifreeze agent without any significant uptake of the stably suspended monensin from the aqueous system into the organic antifreeze agent. This is despite the fact that an organic solvent, such as methanol, allows monensin to crash out of solution if any water is added.

An organic antifreeze agent is deemed desirable in any such aqueous base suspension concentrate since frequently such concentrates are stored in sheds that are subject to extreme variations in temperature including temperatures below the freezing point of the aqueous system unless enhanced with a antifreeze agent.

Any freezing and thawing of the mixture is deemed undesirable as it may affect the uniformity of the monensin or other ionophore antibiotic distribution in the aqueous system. Thus the desirability of the inclusion of an antifreeze agent.

The present invention therefore in at least one aspect is directed to an aqueous base suspension concentrate that can stably support an ionophore antibiotic, or mixtures thereof, with at least the majority of the antibiotic(s) being within the aqueous system and not in any organic inclusion that has been added in as an antifreeze agent.

We have also found (irrespective of whether or not any antifreeze agent is present) that an ionophore antibiotic (such as monensin) can be stably suspended in aqueous suspension by Xanthan Gum that (i) holds the suspension stable when not subjected to shear but which shear thins, (ii) does not significantly age thicken, (iii) is capable of stably supporting a wide range of trace elements of biological significance (especially if in a chelated form) and (iv) is microbiologically stable.

The present invention therefore envisages an aqueous base suspension concentrate that stably supports an ionophore antibiotic, or mixtures thereof, at least in part with Xanthan Gum.

We have also found that as a wetting agent for enabling the mixing of an ionophore antibiotic (especially such as monensin) was much easier using an alkyl polyglycoside over other wetting agents.

The present invention therefore envisages an aqueous base suspension concentrate that stably supports an ionophore antibiotic, or mixtures thereof, where at least some of the antibiotic was mixed with water in the presence of alkyl polyglycoside.

It is believed that an aqueous based suspension concentrate in accordance with the present invention together with its diluted form and its use will provide the public with a useful choice.

In a first aspect the invention consists in an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic (preferably in a crystalline and/or mycelial form) in (II) an aqueous system containing
  (i) a wetting and/or surfactant agent
  (ii) an antifreeze agent or agents in which the ionophore antibiotic or antibiotics is or are no more than sparingly soluble,
  (iii) a suspension agent (preferably with Theological properties),
  (iv) optionally an antifoam agent or system,
  (v) optionally a preservative
  (vi) optionally a de-bittering agent,
  (vii) optionally a pH buffering system, and
  (viii) water.

Preferably one or more (preferably all) of (II) (iv), (v), (vi) and (vii) are present.

In a second aspect the invention consists in an aqueous base suspension concentrate of an ionophore antibiotic or ionophore antibiotics capable of aqueous dilution (if desired) and capable (with or without such aqueous dilution)

of being orally administered to an animal (eg; by drenching), said concentrate comprising (I) at least one ionophore antibiotic (preferably in a crystalline and/or mycelial form) in (II) an aqueous system containing
  (i) a wetting and/or surfactant agent
  (ii) optionally an antifreeze agent or agents in which the ionophore antibiotic or antibiotics is or are no more than sparingly soluble,
  (iii) a suspension agent (preferably with Theological properties),
  (iv) as an antifoam agent or system, Simethicone and a particulate carrier therefor (preferably silicon dioxide)
  (v) optionally a preservative
  (vi) optionally a de-bittering agent,
  (vii) optionally a pH buffering system, and
  (viii) water.

Preferably one or more (preferably all) of (II) (ii), (v), (vi) and (vii) are present.

Preferably (i) is alkyl poyglycoside.

Preferably (ii) is a glycole.

Preferably (iii) is Xanthan Gum.

In a third aspect the invention consists in an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic (preferably in a crystalline and/or mycelial form) in (II) an aqueous system containing
  (i) optionally a wetting and/or surfactant agent
  (ii) optionally an antifreeze agent or agents in which the ionophore antibiotic or antibiotics is or are no more than sparingly soluble,
  (iii) a suspension agent (preferably with Theological properties),
  (iv) an antifoam agent or system, (preferably Simethicone and a particulate carrier therefor),
  (v) optionally a preservative
  (vi) optionally a de-bittering agent,
  (vii) optionally a pH buffering system, and
  (viii) water.

Preferably one or more (preferably all) of (II) (i), (ii), (v), (vi) and (vii) are present.

Preferably (i) is alkyl glycose.

Preferably (ii) is a glycol.

Preferably (iii) is Xantham Gum.

In a fourth aspect the invention consists in an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic (preferably in a crystalline and/or mycelial form) in (II) an aqueous system containing
  (i) optionally a wetting and/or surfactant agent
  (ii) optionally an antifreeze agent or agents in which the ionophore antibiotic or antibiotics is or are no more than sparingly soluble,
  (iii) as a suspension agent (Xanthan Gum).
  (iv) an antifoam agent or system, (preferably Simethicone and a particulate carrier therefor),
  (v) optionally a preservative
  (vi) optionally a de-bittering agent,
  (vii) optionally a pH buffering system, and
  (viii) water.

Preferably said ionophore antibiotic(s) is (are) present in an amount (amounts) effective (A) in beef and dairy cattle, in the treatment or prevention of Ketosis and/or bloat, in the enhancement of milk production, enhancement of milk protein content in milk, enhancement of mineral uptake, enhancement of weight gain, and/or enhancement of feed conversion efficiency in the treatment or prevention of coccidiosis, and/or in effecting reproduction advantages, and/or (B) in calves for any of the purposes of (A) and/or as, at least in part a milk replacer or additive, and/or in the treatment or prevention of coccidiosis, and/or (C) in a runminant, for combination with and/or substantially simultaneous co-administration with other drench components (eg; trace elements, MgO, magnesium salts, zinc salts, pluronics, alcohol ethoxylates, and other metabolic additives) while exhibiting a sufficiently effective role selected from (A) and/or (B).

Preferably said ionophore antibiotic is selected from group consisting of Monensin, Lonomycin, Ionomycin, Laidlomycin, Nigericin, Grisorixin, Dianemycin, Lenoremycin, Salinomycin, Narasin, Antibiotic X206, Alborixin, Septamycin, Antibiotic A204, Compound 47224, Lasalocid (also including factors A, B, C, D and E), Mutalomycin, Isolasalocid A, Lysocellin, Tetronasin, Echeromycin, Antibiotic X-14766A, Antibiotic A23187, Antibiotic A32887, Compound 51532 and K41.

Preferably said ionophore antibiotic is Monensin.

Preferably said Monensin is Sodium Monensin.

Preferably the amount of the ionophore antibiotic is from 3%w/v to 50%w/v (preferably 3–20%w/v and most preferably about 6%w/v).

Preferably the antifreeze agent or agents is a glycol.

Preferably said glycol is monopropylene glycol.

Preferably said glycol is not introduced into the concentrate during its formulation until after substantial stability of the ionophore antibiotic(s) has (have) already been established in the water or at least some of the water.

In still a further aspect the invention consists in an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic (preferably in a crystalline non-mycelial form) in (II) a primarily aqueous system, the concentrate having been prepared by suspending the antibiotic(s) in the primarily aqueous system prior to the addition of all of an organic (preferably glycol) antifreeze agent thereto.

In yet a still further aspect the invention consists in an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic (preferably in a crystalline non-mycelial form) suspended in (II) a primarily aqueous system by a Xanthan Gum suspension agent.

Preferably the primarily aqueous system includes a Simethicon (and carrier therefor) antifoam agent.

Preferably the antifoaming agent system is Simethicone and Silicon Dioxide (premixed together).

Preferably the aqueous system II includes a pH buffering system.

Preferably the buffering system is a phosphate buffering system.

Preferably the buffering system is Disodium Phosphate Anhydrous and Monopotassium phosphate Dihydrate.

Preferably said ionophore antibiotic(s) is (are) present in an amount (amounts) effective (A) in beef and dairy cattle, in the treatment or prevention of ketosis and/or bloat, in the enhancement of milk production, enhancement of milk protein content in milk, enhancement of mineral uptake, enhancement of weight gain, and/or enhancement of feed conversion efficiency in the treatment or prevention of coccidiosis, and/or in effecting reproduction advantages, and/or (B) in calves for any of the purposes of (A) and/or as, at least in part a milk replacer or additive, and/or in the treatment or prevention of coccidiosis, and/or (C) in a ruminant, for combination with and/or substantially simultaneous co-administration with other drench components while exhibiting a sufficiently effective role selected from (A) and/or (B).

Preferably said ionophore antibiotic is selected from group consisting of Monensin, Lonomycin, Ionomycin, Laidlomycin, Nigericin, Grisorixin, Dianemycin, Lenoremycin, Salinomycin, Narasin, Antibiotic X206, Alborixin, Septamycin, Antibiotic A204, Compound 47224, Lasalocid (also including factors A, B, C, D and E), Mutalomycin, Isolasalocid A, Lysocellin, Tetronasin, Echeromycin, Antibiotic X-14766A, Antibiotic A23187, Antibiotic A32887, Compound 51532 and K41.

Preferably said ionophore antibiotic is Monensin.

Preferably said Monensin is Sodium Monensin.

Preferably the amount of the ionophore antibiotic is from 3%w/v to 50%w/v (preferably 3–20%w/v and most preferably about 6.2%w/v).

Preferably the aqueous system II includes an antifreeze agent or agents (preferably a glycol).

Preferably said glycol is monopropylene glycol.

Preferably said glycol is not fully introduced into the aqueous system until after substantial stability of the ionophore antibiotic(s) has (have) already been established in the water or at least some of the water of the aqueous system.

Preferably the aqueous system II includes a preservative (preferably with wetting properties eg; Dialkyl dimethyl ammonium bromide).

Preferably the aqueous system II includes a wetting agent/surfactant (preferably added to water prior to addition of the antibiotic(s)).

Preferably the concentrate is

| | | |
|---|---|---|
| Sodium Monensin (QA331Z) | 3%–50% w/v | Ionophore antibiotic |
| Monopropylene glycol | 1%–20% w/v | Antifreeze |
| Disodium Phosphate Anhydrous | 0%–1% w/v | Buffer |
| MonoPotassium phosphate Dihydrate | 0%–0.5% w/v | Buffer |
| Dialkyl dimethyl ammonium bromide | 0%–0.1% w/v | Preservative |
| Sorbitol | 0%–10% w/v | Debittering agent |
| Xanthan Gum | 0.05%–5% w/v | Suspension agent |
| Alkyl Polyglycoside | 0.05%–2% w/v | Surfactant/ Wetting agent |
| Simethicone | 0.05%–2% w/v | Anti-foam |
| Silicon Dioxide | 0.01%–1% w/v | Carrier for Simethicone |
| Water to 100% | | | and most preferably is

| | | |
|---|---|---|
| Sodium Monensin | about 6% w/v | Ionophore antibiotic |
| Monopropylene glycol | about 10% w/v | Antifreeze |
| Disodium Phosphate Anhydrous | about 0.355% w/v | Buffer |
| MonoPotassium phosphate Dihydrate | about 0.04% w/v | Buffer |
| Dialkyl dimethyl ammonium bromide | about .0064% w/v | Preservative |
| Sorbitol | about 3.5% w/v | Debittering agent |
| Xanthan Gum | about 0.4% w/v | Suspension agent |
| Alkyl Polyglycoside | about 0.5% w/v | Surfactant/ Wetting agent |
| Simethicone | about 0.333% w/v | Anti-foam |
| Silicon Dioxide | about 0.167% w/v | Carrier for Simethicone |
| Water to 100% | | |

Depending on Sodium Monensin batch purity actual amounts required to provide an effective 6%w/v have been 6.24%w/v and 6.33%w/v.

An alternative antifoam agent to the simethicone/silicon dioxide system is a dimethyl polysiloxane/polyoxyalkylene system [silicone glycols]. Where such an alternative is used quantities utilised are substantially as previously stated.

In still a further aspect the present invention consists in an aqueous base suspension concentrate of an ionophore antibiotic or ionophore antibiotics (preferably sodium monensin) capable of aqueous dilution (if desired) and capable (with or without such aqueous dilution) of being orally administered to an animal (eg; by drenching), said concentrate comprising the at least one ionophore antibiotic (preferably in a crystalline non-mycelial form) in an aqueous system which includes an organic antifreeze agent or agents but where most of the antibiotic is suspended in the aqueous system rather than dissolved in the organic antifreeze agent, the antibiotic being supported by a suspension agent.

Preferably said suspension agent is Xanthan Gum.

Preferably said aqueous fraction includes at least one or more of a wetting, buffering, preservative and antifoam and debittering agent.

In still a further aspect the present invention consists in an aqueous base suspension concentrate of an ionophore antibiotic or ionophore antibiotics (preferably sodium monensin) capable of aqueous dilution (if desired) and capable (with or without such aqueous dilution) of being orally administered to an animal (eg; by drenching), said concentrate comprising the at least one ionophore antibiotic (preferably in a crystalline non-mycelial form) in an aqueous system which includes an organic antifreeze agent or agents but where most of the antibiotic is suspended in the aqueous system rather than dissolved in the organic antifreeze agent, the antibiotic being supported by a suspension agent wherein said antibiotic has been mixed into at least some of the water in the presence of a wetting agent and subsequently has been supported as a suspension by the suspension agent.

In still a further aspect the invention consists in a method of preparing an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic in (II) an aqueous system containing (i) a wetting and/or surfactant agent (ii) an antifreeze agent or agents in which the ionophore antibiotic or antibiotics is or are no more than sparingly soluble, (iii) a suspension agent, (iv) optionally an antifoam agent or system, (v) optionally a preservative, (vi) optionally a de-bittering agent, (vii) optionally a pH buffering system, and (viii) water, which comprises
 mixing the antibiotic to an aqueous system already containing at least some of the antifreeze agent(s), the optional preservative (if present and having a wetting effect), and the antifoaming agent or system, and
 subsequently mixing in the balance of components (optionally with some measure of premixing).

Preferably the method of preparation is substantially as herein after described.

The invention also consists in a concentrate so made.

In still a further aspect the present invention consists in as a drench a diluted version of an aqueous base suspension concentrate in accordance with the present invention.

In yet a further aspect the present invention consists in a method of treating an animal (preferably a ruminant animal) for any one or more of the conditions previously set forth or for any of the purposes previously set forth and/or as hereinafter described which comprises administering to the animal orally, or allowing self administration orally, of an aqueous base suspension concentrate in accordance with the present invention or a water diluted version thereof.

Preferably said administration is by means of drenching, eg; preferably using drenching apparatus.

Preferably said administration is of sodium monensin at a daily rate per ruminant animal of from 0.4 milligrams per Kg body weight of animal to 2 milligrams per Kg body weight of animal.

Reference herein to formulations does not rule out the inclusion therein of compatible other inclusions such as essential minerals etc that can usefully be administered simultaneously with the ionophore antibiotic(s). See for example Australian Patent Specification No. 270639 filed 6 Mar. 1995.

Preferred forms of the present invention will now be described with reference (where appropriate) to the accompanying drawings in which.

Preferred forms of the present invention will be described with reference to monensin. With particular reference to crystalline sodium monensin about a 6%w/v inclusion is referred to. This equates to about 6.33%w/v commercially available sodium monensin) because of impurities. Other ionophore antibiotics have been stabilised using corresponding quantities of alternative ionophore antibiotics.

It has primarily been the intention however to utilise sodium monensin and solubilising of the monensin was rejected as was the formation of a wettable powder formulation in favour of a very stable aqueous base suspension.

In evolving the formulations of the present invention a great number of different wetting agents were tried to ensure an adequate wetting of the monensin when being mixed with water. In this respect lecithins, sodium lauryl sulphate, sodium dodecyl sulphate and marlon was tried. Lecithins did not work well, sodium lauryl sulphate and marlon did work but were found not to be as effective as wetting agents as alkyl polyglycoside.

Attempts to solubilise monensin in an organic solvent such as methylated spirits prior to introduction to water was rejected owning to the effect that the alcohols had on at least some suspension agents, ie. guar gum when added was precipitated out by the presence of the organic solvent. Yet when monensin in methylated spirits was added to the water alone the monensin itself precipitated out.

Attempts were made to utilise $Mg(OH)_2+AL(OH)_3$ but it was found that the use thereof in conjunction with monensin led to inadequate suspension of the monensin in the aqueous phase.

Notwithstanding the reference above to attempts to use lecithins as wetting agents, lecithin type compounds such as Emulfid E, Blendmax 322 and Yellinol P were used as wetting agents for the monensin. Some were enzyme modified compounds utilised with a view to modifying the Hydrophilic/Lipophilic balance (ie. HLB) of the compounds. Notwithstanding such attempts as indicated earlier the lecithins did not allow for an optimum wetting of monensin when compared with, by way of example alkyl polyglycoside. Moreover the lecithins tended to be oily and powdered lecithins were expensive.

Cellulose type compounds such as methocel and cellogen were also utilised as possible thickeners in an attempt to hold monensin in aqueous suspension. Some separation was found with such cellulose type compounds with the monensin settling out. Such cellulose type compounds were prone also to age thickening as also was the case with guar gum.

Other suspension agents and wetting agents were utilised, for example, liposorb. Nothing however was located that was as effective as a wetting agent as alkyl polyglycoside nor as effective as a suspension agent as xantham gum.

The present invention relates to an aqueous base suspension concentrate capable of being diluted and administered by a drench gun, such as for example, the DRENCHMATIC™ of Instrument Supplies of Comer Bryant Road and Vickery Street, Te Rapa, Private Bag 3126, Hamilton, New Zealand or the PNEUMEDIC™ Drench Gun System of Enineering Dynamics Ltd of PO Box 30-812, Lower Hutt, New Zealand.

In each of these systems it is possible to administer a diluted version of the aqueous base suspension concentrate of the present invention. The present invention relates to a stable suspension having a shelf life sufficient to allow dilution and then drench administration for an extended period with a minimum of mixing difficulties at the time of dilution and little in the way of metering difficulties to ensure an effective dosage of the ionophore antibiotic is being given.

The preferred suspension in accordance with the present invention is as follows

| | | |
|---|---|---|
| Sodium Monensin | 6.33% (about 6%) w/v | Ionophore-antibiotic |
| Monopropylene glycol | 10% w/v | Antifreeze |
| Disodium Phosphate Anhydrous | 0.355% w/v | Buffer |
| MonoPotassium phosphate Dihydrate | 0.04% w/v | Buffer |
| Dialkyl dimethyl ammonium bromide | .0064% w/v | Preservative |
| Sorbitol | 3.5% w/v | Debittering agent |
| Xanthan Gum | 0.4% w/v | Suspension agent |
| Alkyl Polyglycoside | 0.5% w/v | Surfactant/Wetting agent |
| Simethicone | 0.333% w/v | Anti-foam |
| Silicon Dioxide | 0.167% w/v | Carrier for Simethicone |
| Water to 100% | | |

Previously was set out have options for the components of the concentrate and choices available including in respect of the antibiotic. The preferred form of the present invention however administers monensin and specifically sodium monensin in its crystalline form.

Crystalline monensin can be prepared in a number of different ways. Such a product is available from Eli Lilly & Co, Indianapolis, USA or can be prepared by way of the procedures set out, by way of example, in U.S. Pat. No. 4,213,966 (E.R. Squibb & Sons Inc).

For stability of the ionophore antibiotic an alkaline pH and preferably one about 8–8.2 is desired. The phosphate solvent system preferably buffers for this pH range.

The concentrates of the present invention has a stable shelf life of at least six months and can be decanted in metered amounts at anytime over its shelf life.

The components:

1. Antifreeze Agent (optional in some formulations)

Monoprolene glycol (MPG). It was found that it functioned adequately as an antifreeze.

Was useful to dissolve as a "premix" with DDAB (dialkyl dimethyl ammonium bromide—a preservative with some wetting agent characteristics) and xanthan gum (the preferred aqueous suspension agent for monensin).

Monensin was only very sparingly soluble in MPG without ultrasonic mixing and/or heating.

Other antifreeze agents can be utilised and it would be envisaged that in this respect many glycerol derivatives or mixtures there of could equally be chosen. Care however must be exhibited since a gylcol (such as ethylene glycol) can be very toxic to monogastrics and cause kidney damage.

Since MPG works well and is safe and well known and used in the animal health industry, it is the antifreeze of choice.

2. The Suspension Agent

The suspension of choice is xantham gum, (a hydrocolloid) which has the advantage of locking the suspension when not mobilised but soon as movement is required it shear thins. Unlike many other gums, it also does not age thicken.

Xanthan gum was found to be far more effective than guar gum and other such gums which tended to produce a solid lump in the bottom of the container after a period of time.

Xanthan gum was also very stable with respect to ions such as MGO, ZNO. Moreover xanthan gum is microbiologically stable.

3. The Ionophore Antibiotic

Monensin as sodium monensin was the preferred ionophore antibiotic.

4. The Buffering System

The buffers are of any effective compatible buffering system of a kind set forth.

5. The Preservative

The preservative DDAB was preferably added into the formulation early so as to make best use of its wetting effect in addition to its intended preservative effect. Its presence provides broad spectrum activity from the preservative point of view while at the same time providing some measure of antibloat activity due to its wetting effect.

6. The Wetting Agent

The preferred wetting agent was clearly alkyl polyglycoside. Its molecular structure was most compatible with monensin and enabled monensin to enter the aqueous phase easier than other agents tried. It again is a component to be added early into the preparative process.

7. The Antifoaming Agent

The preferred anti foaming agent is preferably gensil, an emulsion of simethicone and silicon dioxide.

In the examples hereinafter set out of various formulations produced, all percentages are on a w/v basis and in each instance the formulations were of a kind intended to provide an about 3%w/v or about 6%w/v sodium monensin content.

Ingredients: As in each Example.

Equipment: Water deioniser Sanitary pump and connecting hose 2250 liter SS mixing tank (high speed agitator) 50 liter SS vessel Procedure (where ingredients of the Example allows):

1. Preweigh all raw materials, except water, as specified on worksheet.
2. Add approximately 90% of deionised water to stainless mixing tank and turn on high speed stirrer.
3. Add gensil (antifoam), rinse container with deionised water.
4. Add Agrimul 2067. Rinse container with a small amount of deionised water.
5. Preblend, in the 50 liter SS vessel, the DDAB at approximately 1:9 with monopropylene glycol and add to the blender.
6. Slowly add sodium monensin allowing powder to 'wet' before adding more. Once wetted, rinse down sides and stirrer to remove any powder. NB. If sodium monensin is added too quickly lumping may occur.
7. Add disodium phosphate and monopotassium phosphate and stir until dissolved.
8. Add sorbitol and stir until well mixed in (5 minutes).
9. Add 50% of the monopropylene glycol.
10. Preblend, in the 50 liter SS vessel, Rhodigel Supra at approximately 1:3 monopropylene glycol and add to blender with remainder of MPG.
11. Add green dye.
12. Rinse sides and stirrer with deionised water and add balance of water up to mark.
13. Continue stirring until product has thickened and free from lumps (approximately 15–30 minutes). Turn off stirrer. NB. Product will have thickened adequately such that when stirrer is turned off, product will "spring back".

Mix Sequence

The mix sequence is such that preferably (a) DDAB when present is added early but is mixed with monopropelene glycol for adding to the large tank.

(b) The antifoam suspension (preferably gensil) is added early in the sequence to minimise excessive foam being generated by the vigourous mixing required to wet monensin.

The addition of monensin late in the mix sequence is to be avoided as the concentration of monensin achieved with such late addition is far more variable especially when dealing with concentrations greater than 5%w/v. With concentrations of sodium monensin of about 10%w/v it became increasingly difficult to incorporate monensin into the formulation.

Figure 1:
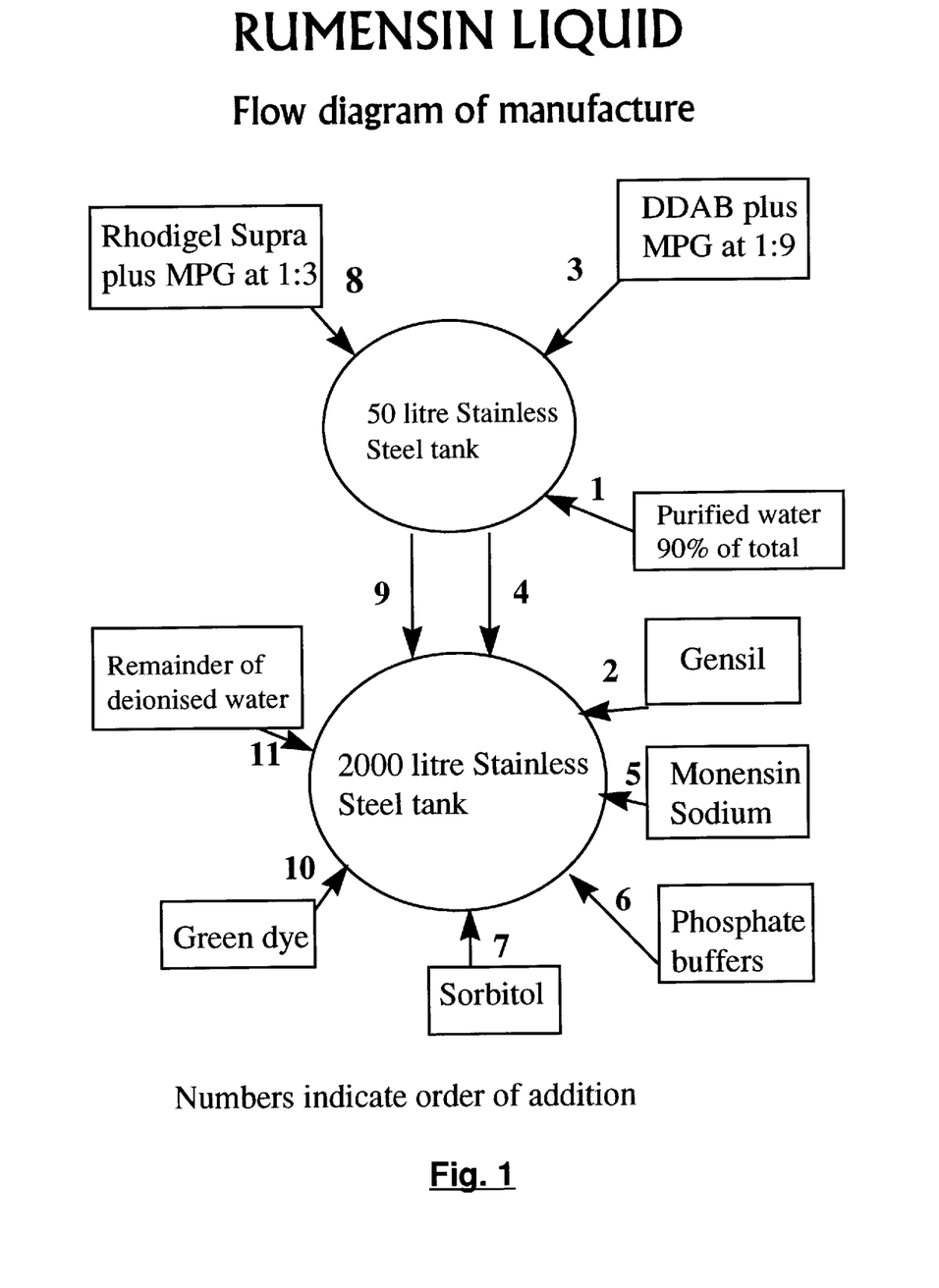
FIG. 1 is a flow diagram showing by reference to the numbers a preferred sequence of addition of specified componentary into one or other of two mixing containers, the numerical sequence being the order of addition.

The preferred sequence for a composition as previously stated or as set out in, for example, Example 17 is as described in FIG. 1.

| Example 1 | |
|---|---|
| Sodium Monensin | 3.12% |
| Emulfluid E (Enzyme Mod. Lec.) | 2.50% |
| Sodium Carbonate FG | 0.02% |
| Cellogen FSH FI | 1.25% |
| Sodium Monensin | 3.12% |
| Sorbitol 70% USP FI | 14.29% |
| Example 2 | |
| Sodium Monensin | 3.12% |
| Yelkinol P | 2.50% |
| Sodium Carbonate FG | 0.02% |
| Cellogen FSH FI | 1.25% |
| Sorbitol 70% USP FI | 14.29% |

Example 3

| | |
|---|---|
| Sodium Monensin | 3.12% |
| Yelkinol P | 2.50% |
| Sodium Carbonate FG | 0.02% |
| Cellogen FSH FI | 0.60% |
| Sorbitol 70% USP FI | 14.29% |

Example 4

| | |
|---|---|
| Sodium Monensin | 3.12% |
| Monopropylene Glycol FI | 5.00% |
| Centrolene S (Hydroxlated LEC) | 10.00% |
| Sodium Carbonate FG | 0.04% |
| Cellogen FSH FI | 1.00% |

Example 5

| | |
|---|---|
| Sodium Monensin | 3.12% |
| Sodium Lauryl Sulphate | 1.60% |
| Guar Gum U | 0.8% |

Example 6

| | |
|---|---|
| Sodium Monensin | 3.12% |
| Sodium Lauryl Sulphate | 0.125% |
| Sipernat 22S | 0.12% |
| Guar Gum U | 0.80% |

Example 7

| | |
|---|---|
| Sodium Monensin | 3.12% |
| Sodium Lauryl Sulphate | 0.125% |
| Sipernat 22S | 0.12% |
| Guar Gum U | 0.80% |

Example 8

| | |
|---|---|
| Sodium Monensin | 3.12% |
| Sodium Lauryl Sulphate | 0.125% |
| Monopropylene Glycol FI | 10.00% |
| Xanthan Gum | 0.16% |

Example 9

| | |
|---|---|
| Sodium Monensin | 3.12% |
| Sodium Lauryl Sulphate | 0.50% |
| Monopropylene Glycol FI | 10.00% |
| Xanthan Gum | 0.2% |

Example 10

| | |
|---|---|
| Sodium Monensin | 3.12% |
| Sodium Lauryl Sulphate | 0.50% |
| Monopropylene Glycol FI | 7.50% |
| Sorbitol 70% USP FI | 5.00% |
| Xanthan Gum 2% Solution | 0.25% |

Example 11

| | |
|---|---|
| Sodium Monensin | 6.24% |
| Sodium Lauryl Sulphate | 0.10% |
| Monopropylene Glycol FI | 8.00% |
| Sorbitol 70% USP FI | 1.00% |
| Xanthan Gum 2% Solution | 0.2% |
| Alkyl Polyglycosides | 0.20% |
| Antifoam Powder | 0.20% |
| Water | 79.876% |

Example 12

| | |
|---|---|
| Sodium Monensin | 3.12% |
| Sodium Lauryl Sulphate | 0.50% |
| Monopropylene Glycol FI | 7.50% |
| Sorbitol 70% USP FI | 5.00% |
| Xantham Gum 2% Solution | 0.4% |

Example 13

| | |
|---|---|
| Sodium Monensin | 3.12% |
| Sodium Lauryl Sulphate | 0.50% |
| Monopropylene Glycol FI | 7.50% |
| Sorbitol 70% USP FI | 5.00% |
| Xantham Gum 2% Solution | 0.3% |

Example 14

| | |
|---|---|
| Sodium Monensin | 3.12% |
| Sodium Lauryl Sulphate | 0.50% |
| Monopropylene Glycol FI | 7.50% |
| Propyl Paraben FI | 0.125% |
| Sodium Monensin | 3.12% |
| Methyl Paraben FI | 0.125% |
| Sorbitol 70% USP FI | 5.00% |
| Xantham Gum 2% Solution | 0.4% |

Example 15

| | |
|---|---|
| Sodium Monensin | 3.12% |
| Sodium Lauryl Sulphate | 0.25% |
| Monopropylene Glycol FI | 7.50% |
| Disodium Phosphate Anhyd FI | 0.36% |
| Dipotassium Phosphate DI FI | 0.0064% |
| Bromosept (DDAB 80) | 0.01% |
| Sorbitol 70% USP FI | 5.00% |

Example 16

| | |
|---|---|
| Sodium Monensin | 6.5% |
| Monopropylene Glycol FI | 7.5% |
| Disodium Phosphate Anhyd FI | 0.355% |
| Dipotassium Phosphate DI FI | 0.04% |
| Bromosept (DDAB 80) | 0.0064% |
| Sorbitol 70% USP FI | |
| Xanthan Gum 2% Solution | 0.4% |
| Alkyl Polyglycosides | 0.5% |
| Antifoam Powder | 0.5% |
| Water | 79.5586% |

Example 17

| | |
|---|---|
| Sodium Monensin | 6.32% |
| Monopropylene Glycol FI | 100.0% |
| Disodium Phosphate Anhyd FI | 0.255% |
| Monopotassium Phosphate DI FI | 0.040% |
| Bromosept (DDAB 80) | 0.0064% |
| Sodium Monensin | 6.32% |
| Sorbitol 70% USP FI | 5.0% |
| Xantham (Rhodigel Supra) FI | 0.40% |
| Agrimul APG 600 | 0.50% |
| Antifoam Powder | 0.50% |
| Water | 76.8786% |

Report on Performance of 6% (Nominal) Monensin Suspension in Drenching Systems

In all in vivo tests 1 liter of 6% monensin composition (as in Example 17) was added to 19 liters of water in the powder drenching system reservoir. This equates to a drenching rate of 100 mls of drench providing 300 mg monensin per day. The monensin suspension dispersed easily with a low level of foaming even on full agitation with the submersible pump on full by-pass.

1. To the 20 liters of monensin suspension was added the equivalent amount of nonylphenol ethoxylate (Blocare 4511) for dosing 200 cows at the rate of 5 mls/cow. The foam level increased dramatically but this was due to the Blocate.

No chemical reactions were observed.

2. To another 20 liter batch of monensin suspension was added 4 kg of magnesium oxide (calmag). There was a slight increase in foam level but not more than is normal for calmag on its own. No chemical reactions were observed.

3. To another 20 liter batch of monensin suspension was added 20 kg of magnesium chloride flake. There was no significant increase in foam. There was some sediment in the bottom of the reservoir on emptying. This was a mixture of undissolved $MgCl_2$ residual CALMAG™ (ie. MgO) and rust). There did not appear to be any chemical reactions.

General Comments

Larger particles only of sodium monensin was seen to settle out 15 to 20 minutes after agitation cease. These particles re-suspended easily upon recommencement of liquid flow through the tubing (ie. agitation).

The settling out of the monensin was not considered to be a major problem because of the ease of re-suspension of the monensin, once re-agitated the degree of agitation provided by a power drench system by emptying the drench line prior to the start of a row of animals to be drenched the probability of an animal receiving more than two times the required dosage of monensin within the 100 ml volume is very low.

Evaluation of the effectiveness of 100 ml/day of Composition of 6%w/v sodium monensin to control bloat in milking cows on pasture Two trials were carried out in September/October 1995 to evaluate the effectiveness of 100 ml/day of the Example 17 composition as a drench to control bloat in milking cows on pasture, firstly by drenching 50 ml twice a day, ie. before each milking (Trial 1A), and secondly, by drenching 100 ml before each morning milking (Trial 1B). There was 300 mg active ingredient administered per day. In each Trial half of the 30 cows were allocated by restricted random allocation to the untreated Control group, and half to the Liquid Product ('treated') group. Animals were scored for bloat twice daily on white clover/ryegrass pastures or on red clover pastures (using a scale of 0, 1, 1.5, 2, 2.5, 3, representing scores of increasing severity of bloat, by assessing pressure on the cows' left and right sides).

In Trial 1A, serious bloat was recorded on 9 mornings out of 23 am and pm recording sessions. Twelve of 15 cows from the Control group were at risk of death from bloat (if left untreated) on at least one day, compared with 3 of 15 in the Treated group, a statistically significant difference (P<0.01). Mean scores on 8 bloating days were respectively 0.58 and 0.12 which was a significant difference (P<0.01). On the most serious four bloat days, corresponding scores were 0.94 and 0.20 (also a significant difference at P<0.01).

In Trial 1B, 3 serious bloat sessions out of 9 am and pm recording sessions led to 8/15 Control animals being at risk, compared with 1/14 Treated animals (a statistically significant difference, P<0.01). Mean scores on these 3 bloating days were 0.65 and 0.10 respectively, representing a statistically significant difference between groups (P<0.01).

The composition of Example (17) was successful in reducing the mean bloat score and the number of animals at risk.

Trial 1A 9/25 to 10/6/95 Treatment=50 ml liquid Composiiton of 6%w/v sodium monensin twice a day

TABLE 1

Mean bloat score on days when bloat was recorded (treated and control)

| Day | Mean Score | Number of cows at risk (ie. A score $\geq 1.5$) |
|---|---|---|
| 1 | 0.27 | 4 |
| 3 | 0.08 | 1 |
| 4 | 0.08 | 1 |
| 5 | 0.09 | 1 |
| 8 | 0.18 | 1 |
| 9 | 0.70 | 9 |
| 10 | 0.85 | 11 |
| 11 | 0.37 | 5 |
| 12 | 0.47 | 5 |
| Mean/Total | 0.34 | 15[a] |

[a]Excluding Day 1, where equilibration in the rumen may not have been reached.

TABLE 2

Treatment effects on bloat-score means from all nine days when bloat was recorded, and from subsets of days

| Number of score days | Non-treated | Treated | s.e.d. | Signif.[b] | Phenotypic s.d.[c] |
|---|---|---|---|---|---|
| 9[a] | 0.55 | 0.13 | 0.13 | ** | 0.60 |
| 8 (excluding first) | 0.568 | 0.12 | 0.13 | ** | 0.59 |
| Best 4 | 0.94 | 0.20 | 0.20 | ** | 0.73 |
| The Other 4 | 0.30 | 0.07 | 0.10 | * | 0.49 |

[a]Between-cow repeatability = 0.28 ± 0.07 (9 days); 0.45 ± 0.10 (best 4 days).
[b]* = P < 0.05; ** = P < 0.01.
[c]From the cow and residual variance components combined.

TABLE 3

Numbers of bloated animals by treatment (15 per group), using various criteria of bloat

| Criterion | Non-treated | Treated | Chi-square | Signif.[b] |
|---|---|---|---|---|
| Cows with a mean of 0 on Days 9–12 | 2 | 11 | 11.00 | *** |
| Cows with a mean $\geq$ on Days 9–12 | 7 | 1 | 6.14 | * |
| Cows at risk (score $\geq$ 1.5) on at least one day[a] | 12 | 3 | 10.80 | ** |

[a]Excluding Day 1, where equilibration in the rumen may not have been reached.
[b]* = P < 0.05; II + P < 0.01; *** = P < 0.001.

Trial 1B 10/24 to 10/28/95 Treatment=100 ml liquid composition of 6%w/v sodium monensin per day in one dose at 0615

TABLE 4

Mean bloat score on days when bloat was recorded

| Day | Mean score | Number of cows at risk (ie. a score $\geq 1.5$) |
|---|---|---|
| 3 | 0.29 | 3 |
| 4 | 0.56 | 7 |
| 5 | 0.27 | 3 |
| Mean/Total | 0.37 | 9 |

TABLE 5

Treatment effects on bloat score means from Days 3 to 5.

| Trait | Non-treated | Treated | s.e.d. | Signif.[a] | Phenotypic[b] s.d. |
|---|---|---|---|---|---|
| Bloat score | 0.65 | 0.10 | 0.15 | *** | 0.60 |
| Number at risk (score $\geq$ 1.5) | 8 | 2 | 7.20[c] | ** | |

[a] = P < 0.01; * = P < 0.001.
[b]Between-cow repeatability = 0.18 ± 0.12 (3 days); the phenotypic standard deviation is from the cow and residual components combined.
[c]Chi-square, testing 8/15 against 1/14.

What we claim is:

1. An aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic in (II) an aqueous system containing (i) a wetting and/or surfactant agent (ii) an antifreeze agent or agents in which the ionophore antibiotic or antibiotics is or are no more than sparingly soluble,
(iii) a suspension agent,
(iv) optionally an antifoam agent or system,
(v) optionally a preservative,
(vi) optionally a de-bittering agent,
(vii) optionally a pH buffering system, and
(viii) water.

2. A concentrate of claim 1 wherein one or more of (II) (iv), (v), (vi) and (vii) are present.

3. A concentrate of claim 1 or 2 wherein (i) is alkyl polyglycoside.

4. A concentrate of claim 1 or 2 wherein (ii) is a glycol.

5. A concentrate of claim 1 or 2 wherein (iii) is Xanthan Gum.

6. An aqueous base suspension concentrate of an ionophore antibiotic or ionophore antibiotics capable of aqueous dilution (if desired) and capable (with or without such aqueous dilution) of being orally administered to an animal, said concentrate comprising
(I) at least one ionophore antibiotic in (II) an aqueous system containing
(i) a wetting and/or surfactant agent
(ii) optionally an antifreeze agent or agents in which the ionophore antibiotic or antibiotics is or are no more than sparingly soluble,
(iii) a suspension agent,
(iv) as an antifoam agent or system, Simethicone and a particulate carrier therefor,
(v) optionally a preservative,
(vi) optionally a de-bittering agent,
(vii) optionally a pH buffering system, and
(viii) water.

7. A concentrate of claim 6 wherein one or more of (II) (ii), (v), (vi) and (vii) are present.

8. A concentrate of claim 6 or 7 wherein (i) is alkyl glycoside.

9. A concentrate of claim 6 or 7 wherein (ii) is a glycol.

10. A concentrate of claim 6 or 7 wherein (iii) is Xanthan Gum.

11. An aqueous base suspension concentrate of an ionophore antibiotic or ionophore antibiotics capable of aqueous dilution (if desired) and capable (with or without such aqueous dilution) of being orally administered to an animal, said concentrate comprising
(I) at least one ionophore antibiotic (preferably in a crystalline and/or mycelial form) in (II) an aqueous system containing
(i) optionally a wetting and/or surfactant agent
(ii) optionally an antifreeze agent or agents in which the ionophore antibiotic or antibiotics is or are no more than sparingly soluble,
(iii) a suspension agent,
(iv) an antifoam agent or system,
(v) optionally a preservative,
(vi) optionally a de-bittering agent,
(vii) optionally a pH buffering system, and
(viii) water.

12. A concentrate of claim 11 wherein one or more of (II) (i), (ii), (v), (vi) and (vii) are present.

13. A concentrate of claim 11 or 12 wherein (iii) is Xanthan Gum.

14. A concentrate of claim 11 or 12 wherein (iv) is a Simethicone and a particulate carrier therefor.

15. An aqueous base suspension concentrate of an ionophore antibiotic or ionophore antibiotics capable of aqueous dilution (if desired) and capable (with or without such aqueous dilution) of being orally administered to an animal, said concentrate comprising
(I) at least one ionophore antibiotic in (II) an aqueous system containing
(i) optionally a wetting and/or surfactant agent,
(ii) optionally an antifreeze agent or agents in which the ionophore antibiotic or antibiotics is or are no more than sparingly soluble,
(iii) as a suspension agent Xanthan Gum,
(iv) an antifoam agent or system,
(v) optionally a preservative
(vi) optionally a de-bittering agent,
(vii) optionally a pH buffering system, and
(viii) water.

16. A concentrate of claim 15 wherein (iv) is a Simethicone and a particulate carrier therefor.

17. A concentrate of claim 1 wherein said ionophore antibiotic(s) is (are) present in an amount (amounts) effective
(A) in beef and dairy cattle,
in the treatment or prevention of Ketosis and/or bloat,
in the enhancement of milk production, enhancement of milk protein content in milk, enhancement of mineral uptake, enhancement of weight gain, and/or enhancement of feed conversion efficiency in the treatment or prevention of coccidiosis, and/or
in effecting reproduction advantages, and/or
(B) in calves
for any of the purposes of (A), and/or as, at least in part a milk replacer or additive, and/or in the treatment or prevention of coccidiosis, and/or
(C) in a ruminant,
for combination with and/or substantially simultaneous co-administration with other drench components (eg; trace elements, MgO, magnesium salts, zinc salts, pluronics, alcohol ethoxylates, and other metabolic additives) while exhibiting a sufficiently effective role selected from (A) and/or (B).

18. A concentrate of claim 10 wherein said ionophore antibiotic(s) is(are) selected from group consisting of Monensin, Lonomycin, Ionomycin, Laidlomycin, Nigericin, Grisorixin, Dianemycin, Lenoremycin, Salinomycin, Narasin, Antibiotic X206, Alborixin, Septamycin, Antibiotic A204, Compound 47224, Lasalocid (also including factors A, B, C, D and E), Mutalomycin, Isolasalocid A, Lysocellin, Tetronasin, Echeromycin, Antibiotic X-14766A, Antibiotic A23 187, Antibiotic A32887, Compound 51532 and K41.

19. A concentrate of claim 18 wherein said ionophore antibiotic is Monensin.

20. A concentrate of claim 19 wherein said Monensin is Sodium Monensin.

21. A concentrate of any one of claims 18 to 20 wherein the amount of the ionophore antibiotic(s) is from 3%w/v to 50%w/v.

22. A concentrate of claim 21 wherein the amount of ionophore antibiotic(s) is from 3%w/v to 20%w/v.

23. A concentrate of claim 22 wherein the ionophore antibiotic is about 6%w/v sodium monensin.

24. A concentrate of claim 18 wherein the antifreeze agent is monopropylene glycol.

25. An aqueous base suspension concentrate of an ionophore antibiotic or ionophore antibiotics capable of aqueous dilution (if desired) and capable (with or without such aqueous dilution) of being orally administered to an animal, said concentrate comprising
(I) at least one ionophore antibiotic in (II) a primarily aqueous system, the concentrate having been prepared by suspending the antibiotic(s) in the primarily aqueous system prior to the addition of all of an organic antifreeze agent thereto.

26. An aqueous base suspension concentrate of an ionophore antibiotic or ionophore antibiotics capable of aqueous dilution (if desired) and capable (with or without such aqueous dilution) of being orally administered to an animal, said concentrate comprising (I) at least one ionophore antibiotic suspended in (II) a primarily aqueous system by a Xanthan Gum suspension agent.

27. A concentrate of claim 26 wherein the primarily aqueous system includes a Simethicon (and carrier therefor) antifoam agent.

28. A concentrate of claim 27 wherein the antifoaming agent system is Simethicone and Silicon Dioxide (premixed together).

29. An aqueous base suspension concentrate of sodium monensin comprising

| | |
|---|---|
| Sodium Monensin | 3%–50% w/v, |
| Monopropylene glycol | 1%–20% w/v, |
| Disodium Phosphate Anhydrous | 0%–1% w/v, |
| monopotassium phosphate Dihydrate | 0%–0.5% w/v, |
| Dialkyl dimethyl ammonium bromide | 0%–0.1% w/v, |
| Sorbitol | 0%–10% w/v, |
| Xanthan Gum | 0.05%–5% w/v, |
| Alkyl Polyglycoside | 0.05%–2% w/v, |
| Simethicone | 0.05%–2% w/v, |
| Silicon Dioxide | 0.01%–1% w/v, and |

30. A concentrate of claim 21 comprising

| | |
|---|---|
| Sodium Monensin | about 6% w/v, |
| Monopropylene glycol | about 10% w/v, |
| Disodium Phosphate Anhydrous | about 0.355% w/v, |
| monopotassium phosphate Dihydrate | about 0.04% w/v, |
| Dialkyl dimethyl ammonium bromide | about .0064% w/v, |
| Sorbitol | about 3.5% w/v, |
| Xanthan Gum | about 0.4% w/v, |
| Alkyl Polyglycoside | about 0.5% w/v, |
| Simethicone | about 0.333% w/v, |
| Silicon Dioxide | about 0.167% w/v, and |
| Water to 100%. | |

31. An aqueous base suspension concentrate of an ionophore antibiotic or ionophore antibiotics capable of aqueous dilution (if desired) and capable (with or without such aqueous dilution) of being orally administered to an animal, said concentrate comprising the at least one ionophore antibiotic in an aqueous system which includes an organic antifreeze agent or agents but where most of the antibiotic(s) is(are) suspended in the aqueous system rather than dissolved in the organic antifreeze agent, the antibiotic being supported by a suspension agent.

32. A concentrate of claim 31 wherein said suspension agent is Xanthan Gum.

33. A concentrate of claim 31 or 32 wherein Preferably said aqueous fraction includes at least one or more of the group consisting of wetting, buffering, preservative, antifoam and debittering agents.

34. An aqueous base suspension concentrate of an ionophore antibiotic or ionophore antibiotics capable of aqueous dilution (if desired) and capable (with or without such aqueous dilution) of being orally administered to an animal, said concentrate comprising the at least one ionophore antibiotic in an aqueous system which includes an organic antifreeze agent or agents but where most of the antibiotic is suspended in the aqueous system rather than dissolved in the organic antifreeze agent, the antibiotic being supported by a suspension agent wherein said antibiotic has been mixed into at least some of the water in the presence of a wetting agent and subsequently has been supported as a suspension by the suspension agent.

35. A concentrate of claim 34 wherein the antibiotic is a salt of monensin.

36. As a drench a diluted version of an aqueous base suspension concentrate as claimed in claim 34.

37. A method of forming an aqueous base suspension concentrate of an ionophore antibiotic or ionophore antibiotics capable of aqueous dilution (if desired) and capable (with or without such aqueous dilution) of being orally administered to an animal (eg; by drenching), said concentrate comprising (I) at least one ionophore antibiotic in (II) an aqueous system containing
(i) a wetting and/or surfactant agent
(ii) an antifreeze agent or agents in which the ionophore antibiotic or antibiotics is or are no more than sparingly soluble,
(iii) a suspension agent,
(iv) optionally an antifoam agent or system,
(v) optionally a preservative,
(vi) optionally a de-bittering agent,
(vii) optionally a pH buffering system, and
(viii) water, which comprises mixing the antibiotic to an aqueous system already containing at least some of the antifreeze agent(s), the optional preservative (if present and having a wetting effect), and the antifoaming agent or system, and subsequently mixing in the balance of components (optionally with some measure of premixing).

38. A concentrate formed by the method of claim 37.

* * * * *